(12) United States Patent
Fujiwara et al.

(10) Patent No.: US 10,576,197 B2
(45) Date of Patent: Mar. 3, 2020

(54) BLOOD PURIFICATION DEVICE AND PRIMING METHOD

(71) Applicant: NIKKISO CO., LTD., Tokyo (JP)

(72) Inventors: Masato Fujiwara, Makinohara (JP); Yoshimichi Masuda, Makinohara (JP); Hiroshi Nimura, Makinohara (JP); Yoichi Jimbo, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 120 days.

(21) Appl. No.: 15/571,250

(22) PCT Filed: May 11, 2016

(86) PCT No.: PCT/JP2016/063988
§ 371 (c)(1),
(2) Date: Nov. 1, 2017

(87) PCT Pub. No.: WO2016/181989
PCT Pub. Date: Nov. 17, 2016

(65) Prior Publication Data
US 2018/0110914 A1    Apr. 26, 2018

(30) Foreign Application Priority Data
May 12, 2015 (JP) ................. 2015-097414

(51) Int. Cl.
*A61M 1/36* (2006.01)
*A61M 1/16* (2006.01)
(Continued)

(52) U.S. Cl.
CPC ........ *A61M 1/3649* (2014.02); *A61M 1/1694* (2013.01); *A61M 1/267* (2014.02);
(Continued)

(58) Field of Classification Search
CPC .. A61M 1/3649; A61M 1/3644; A61M 1/267; A61M 1/3638; A61M 1/1694;
(Continued)

(56) References Cited

U.S. PATENT DOCUMENTS 5,536,412 A * 7/1996 Ash ............... A61M 1/1696
210/195.1
5,591,344 A 1/1997 Kenley et al.
(Continued)

FOREIGN PATENT DOCUMENTS

CN 103889481 A 6/2014
EP 0 829 265 A1 3/1998
(Continued)

OTHER PUBLICATIONS

Aug. 2, 2016 International Search Report issued in International Patent Application No. PCT/JP2016/063988.
(Continued)

*Primary Examiner* — Joseph W Drodge
(74) *Attorney, Agent, or Firm* — Oliff PLC

(57) ABSTRACT

A blood purification device for purifying blood drawn from a body and then returning the blood into the body, including: a pump provided midway along a fluid path through which blood or a dialysis fluid flows; a valve that is provided midway along the fluid path and closes or opens a part of the fluid path; and a control unit that causes a blood purification process of passing the blood or the dialysis fluid through the fluid path for blood purification, a priming process of driving the pump and the valve to supply a priming fluid to the fluid path before the blood purification processing, and a pressure reduction process of reducing pressure in a gap in the fluid path to a negative pressure state before supply of the priming fluid.

7 Claims, 9 Drawing Sheets

(51) Int. Cl.
*A61M 1/34* (2006.01)
*B01D 61/30* (2006.01)
*B01D 61/32* (2006.01)
*A61M 1/26* (2006.01)

(52) U.S. Cl.
CPC ............ *A61M 1/36* (2013.01); *A61M 1/3638* (2014.02); *A61M 1/3644* (2014.02); *B01D 61/30* (2013.01); *B01D 61/32* (2013.01); *A61M 1/1696* (2013.01); *A61M 2205/3331* (2013.01); *A61M 2205/3337* (2013.01)

(58) Field of Classification Search
CPC .................. A61M 1/36; A61M 1/1696; A61M 2205/3337; A61M 2205/3331; A61M 2205/05; A61M 2205/12; A61M 2205/121; A61M 2205/128; A61M 1/14; A61M 1/16; A61M 1/1601; A61M 1/1621; A61M 1/1629; A61M 1/1635; A61M 1/1637; A61M 1/1649; A61M 1/1658; A61M 1/166; A61M 1/168; A61M 1/28; A61M 1/281; A61M 1/34; A61M 1/3455; A61M 1/3465; A61M 1/3472; A61M 1/3643; A61K 35/407; B01D 61/24; B01D 61/243; B01D 61/26; B01D 61/28; B01D 61/30; B01D 61/32
USPC ...... 604/19, 27–30, 122, 123; 210/175, 180, 210/188, 195.2, 321.6, 321.69, 321.71, 210/636, 646, 647, 805, 806; 95/241, 95/251, 259; 96/155, 218
See application file for complete search history.

(56) References Cited

U.S. PATENT DOCUMENTS

| | | | |
|---|---|---|---|
| 5,766,480 | A | 6/1998 | Cosentino et al. |
| 9,713,665 | B2* | 7/2017 | Meyer ................ B01D 19/0068 |
| 9,855,377 | B2* | 1/2018 | Childers ................ A61M 1/16 |
| 2008/0237128 | A1* | 10/2008 | Rovatti ............... A61M 1/3643 210/646 |
| 2009/0088675 | A1* | 4/2009 | Kelly .................. A61M 1/3627 604/4.01 |
| 2010/0078385 | A1* | 4/2010 | Kawarabata ........... A61M 1/34 210/646 |
| 2011/0213289 | A1 | 9/2011 | Toyoda et al. |
| 2012/0103902 | A1* | 5/2012 | Childers ................. A61M 1/16 210/646 |
| 2013/0150768 | A1 | 6/2013 | Sakamoto et al. |
| 2013/0199998 | A1 | 8/2013 | Kelly et al. |
| 2014/0217029 | A1* | 8/2014 | Meyer ................. A61M 1/3465 210/647 |
| 2015/0283318 | A1* | 10/2015 | Wang .................. A61M 1/3472 210/638 |
| 2015/0367062 | A1* | 12/2015 | Brugger ............. A61M 1/3646 210/646 |
| 2016/0101278 | A1* | 4/2016 | Norris ................... A61M 1/166 604/29 |
| 2017/0143886 | A1* | 5/2017 | Wilt .................... A61M 1/1037 |

FOREIGN PATENT DOCUMENTS

| | | |
|---|---|---|
| EP | 2 168 613 A1 | 3/2010 |
| JP | 2003-199821 A | 7/2003 |
| JP | 2008-012210 A | 1/2008 |
| JP | 2009-285128 A | 12/2009 |
| JP | 2010-125208 A | 6/2010 |
| JP | 5294985 B2 | 9/2013 |
| JP | 2014-525804 A | 10/2014 |
| WO | 2012/017959 A1 | 2/2012 |
| WO | 2014/124180 A2 | 8/2014 |
| WO | 2016/067946 A1 | 5/2016 |

OTHER PUBLICATIONS

Nov. 27, 2018 Extended European Search Report issued in European Patent Application No. 16792714.4.
Oct. 8, 2019 Office Action issued in Chinese Patent Application No. 201680027849.5.
Dec. 10, 2019 Office Action issued in Japanese Patent Application No. 2017-517962.

* cited by examiner

| | | SPEED OF BLOOD PUMP [mL/min] | FEEDING PUMP [mL/min] | FIRST TEST VALVE | SECOND TEST VALVE | AMOUNT OF FLUID [mL] | CONTENTS OF STEP |
|---|---|---|---|---|---|---|---|
| EXAMPLE 1 | STEP1 | -100 | -250 | CLOSE | CLOSE | 0 | REDUCE PRESSURE IN FLUID PATH (-300mmHg) |
| | STEP2 | -100 | 250 | OPEN | CLOSE | 500,1500 | BLOOD SIDE PRIMING (BACKFILTERATION) |
| | STEP3 | 0 | 250 | CLOSE | OPEN | 500 | DIALYSIS FLUID SIDE PRIMING |
| EXAMPLE 2 | STEP1 | -100 | -250 | CLOSE | CLOSE | 0 | REDUCE PRESSURE IN FLUID PATH (-500mmHg) |
| | STEP2 | -100 | 250 | OPEN | CLOSE | 500,1500 | BLOOD SIDE PRIMING (BACKFILTERATION) |
| | STEP3 | 0 | 250 | CLOSE | OPEN | 500 | DIALYSIS FLUID SIDE PRIMING |
| EXAMPLE 3 | STEP1 | -100 | -250 | CLOSE | CLOSE | 0 | REDUCE PRESSURE IN FLUID PATH (-700mmHg) |
| | STEP2 | -100 | 250 | OPEN | CLOSE | 500,1500 | BLOOD SIDE PRIMING (BACKFILTERATION) |
| | STEP3 | 0 | 250 | CLOSE | OPEN | 500 | DIALYSIS FLUID SIDE PRIMING |
| COMPARATIVE EXAMPLE | STEP1 | -100 | 250 | OPEN | CLOSE | 500,1500 | BLOOD SIDE PRIMING (BACKFILTERATION) |
| | STEP2 | 0 | 250 | CLOSE | OPEN | 500 | DIALYSIS FLUID SIDE PRIMING |

FIG. 4

BLOOD PURIFICATION DEVICE AND PRIMING METHOD

TECHNICAL FIELD

The present invention relates to a blood purification device for purifying blood drawn from a body and then returning the blood into the body, and a priming method of supplying a priming fluid to a fluid path through which blood or a dialysis fluid flows before a blood purification processing.

BACKGROUND ART

Conventionally, in dialysis treatment or the like, a blood purification device has been used for purifying and circulating collected patient's blood outside a body and again returning the blood into the body. Such a blood purification device includes a fluid path through which blood or a dialysis fluid flows. The fluid path includes a blood line through which blood flows, a dialysis fluid line through which a dialysis fluid flows, a dialyzer including a hollow fiber membrane (blood purification membrane), and the like. To a distal end of the blood line, an artery side puncture needle and a vein side puncture needle are attached. The puncture needles are inserted into a patient to perform extracorporeal circulation of blood in the dialysis treatment.

Before passing blood or a dialysis fluid through the fluid path, a process called "priming" is typically performed for supplying a priming fluid that is physiological saline or a dialysis fluid into the fluid path to fill the fluid path. The priming process is performed to wash the fluid path, improve wettability, and so on. In such a priming process, in order to remove air remaining in the fluid path, a healthcare personnel taps a dialyzer or a pipe by hand so that attached air bubbles flow. However, such manual removal of air bubbles is troublesome.

CITATION LIST

Patent Literature

Patent Literature 1: Japanese Patent Laid-Open Publication No. 2003-199821
Patent Literature 2: Japanese Patent No. 5294985

SUMMARY OF INVENTION

Technical Problem

Patent Literature 1 discloses a technology of generating a plurality of short pressure pulses into an extracorporeal circulation circuit (blood pipe) in a priming process. Such a technology may remove air bubbles in a pipe to some extent. However, it is difficult to remove air bubbles in a dialyzer only using the pressure pulses applied to the pipe, and the air bubbles tend to remain in the dialyzer.

Patent Literature 2 discloses a technology of reducing pressure in a dialysis fluid flow path of a dialyzer to negative pressure during priming. However, in Patent Literature 2, a priming fluid is drawn into a fluid path, and then negative pressure is produced only in the dialyzer. Thus, it is difficult to remove air outside the dialyzer. Also, for the dialyzer per se, in the case of the technology in Patent Literature 2 of drawing the priming fluid and then reducing pressure, air in the dialyzer is blocked by the priming fluid and cannot be discharged, and thus air in the dialyzer cannot be removed.

The technology in Patent Literature 2 is intended to reduce pressure for allowing a fluid to easily flow into a laminate type dialyzer, and is not intended to remove air. Also, reducing pressure during the priming processing complicates the entire priming process.

Specifically, it has been conventionally difficult to easily and reliably prevent air from remaining in a fluid path during execution of priming. Thus, the present invention has an object to provide a blood purification device and a priming method capable of easily and reliably preventing air from remaining in a fluid path during execution of priming.

Solution to Problem

The present invention provides a blood purification device for purifying blood drawn from a body and then returning the blood into the body, including: a pump provided midway along a fluid path through which blood or a dialysis fluid flows; a valve that is provided midway along the fluid path and closes or opens a part of the fluid path; and a control unit that causes a blood purification process of passing the blood or the dialysis fluid through the fluid path for blood purification, a priming process of driving the pump and the valve to supply a priming fluid to the fluid path before the blood purification processing, and a pressure reduction process of reducing pressure in a gap in the fluid path to a negative pressure state before supply of the priming fluid.

In a preferred aspect, the fluid path includes at least a blood purifier that purifies blood, and a blood line through which the blood flows. In this case, the fluid path desirably further includes an air trap chamber. Also, the blood purifier is desirably a dialyzer that includes a blood purification membrane therein and purifies blood with the blood purification membrane, and the priming fluid is desirably a dialysis fluid backfiltered by the dialyzer.

In another preferred aspect, the pump includes a blood pump that feeds the blood to the blood purifier, a feeding pump that feeds the dialysis fluid to the blood purifier, and a discharge pump that discharges the dialysis fluid from the blood purifier, and the control unit drives the valve to close off the fluid path from outside air, and then performs at least one of the following three functions: reverse driving of the blood pump, driving of the discharge pump, and reverse driving of the feeding pump to reduce pressure in the gap.

In a further preferred aspect, the blood purification device includes a dialysis fluid regeneration column that reproduces the dialysis fluid having passed through the blood purifier and returns the dialysis fluid to the blood purifier to circulate the dialysis fluid.

In a further preferred aspect, the blood purifier is a blood purification column that includes an adsorbent for purifying blood therein and purifies blood. In a further preferred aspect, the pump includes a vacuum pump that is provided midway along the fluid path, sucks air in the fluid path, and does not feed the dialysis fluid and the blood, and the control unit drives the valve to close off the fluid path from outside air, and then drives the vacuum pump to reduce pressure in the gap.

The present invention further provides a priming method of supplying a priming fluid to a fluid path through which blood or a dialysis fluid flows before a blood purification process of purifying blood drawn from a body and then returning the blood into the body, wherein a pump and a valve provided midway along the blood path are driven to reduce pressure in a gap in the fluid path to a negative pressure state before supply of the priming fluid.

In the present invention, the "valve" includes not only a valve provided independently of a pump but also a pump that serves as a valve. For example, a tube pump serves as a pump that feeds a fluid into the flow path, and also serves as a valve that closes the flow path during stop of driving and opens the flow path during driving. In the case of using such a pump, an independently provided valve may be omitted.

Advantageous Effect of Invention

According to the present invention, the pressure reduction process of reducing pressure in the gap in the fluid path to a negative pressure state is performed before the priming process, thereby easily and reliably preventing air from remaining in the fluid path during performance of priming.

BRIEF DESCRIPTION OF THE DRAWINGS

FIG. 4 is a table showing procedures of the verification experiment.

DESCRIPTION OF EMBODIMENTS

Figure 1:
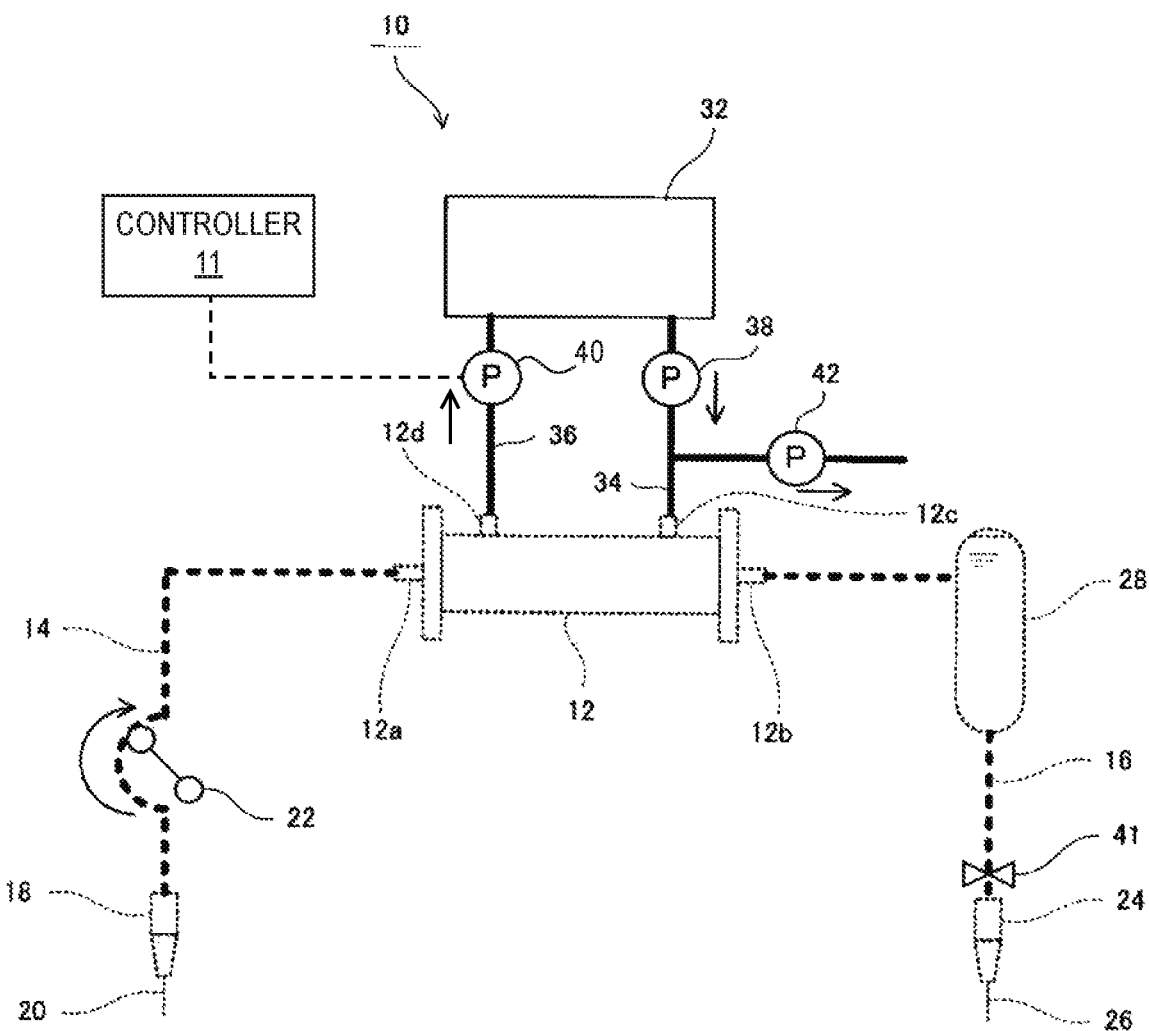
FIG. 1 shows a configuration of a dialysis system according to an embodiment of the present invention.

Now, an embodiment of the present invention will be described with reference to the drawings. FIG. 1 shows a configuration of a dialysis system 10 according to an embodiment of the present invention. Parts shown by solid lines in FIG. 1 are components of the dialysis system 10. Parts shown by dashed lines in FIG. 1 are consumable units discarded and replaced for each use. In FIG. 1, arrows near pumps 22, 38, 40, 42 show directions of normal driving of the pumps. The dialysis system 10 is a blood purification device that brings blood into contact with a dialysis fluid via a hollow fiber membrane (not shown) that is a blood purification membrane provided in a dialyzer 12 to purify the blood. The dialysis system 10 includes a dialysis fluid supply device 32, a blood pump 22, a feeding pump 38, a discharge pump 40, a valve 41, a vacuum pump 42, pipes 34, 36, and the like. The consumable unit includes an artery side blood line 14 and a vein side blood line 16. One end of the artery side blood line 14 and one end of the vein side blood line 16 are connected to a blood inlet 12a and a blood outlet 12b, respectively, of the dialyzer 12 (blood purifier). Depending on a configuration or the like of the device, the pipes 34, 36 may be consumables that are discarded and replaced for each use like the blood lines 14, 16 or the like.

The dialyzer 12 has a substantially cylindrical casing, and the blood inlet 12a and the blood outlet 12b are formed in axially opposite ends of the casing. A dialysis fluid inlet 12c and a dialysis fluid outlet 12d are formed in a peripheral surface of the casing of the dialyzer 12. A plurality of hollow fiber membranes that serve as blood purification membranes are disposed in the casing. An inside of each hollow fiber membrane constitutes a part of a blood path through which blood flows, and a space between an outer peripheral surface of the hollow fiber membrane and an inner peripheral surface of the casing constitutes a part of a dialysis fluid path through which a dialysis fluid flows.

A plurality of minute holes are formed in the hollow fiber membrane, and thus when blood passes through the inside of the hollow fiber membrane and the dialysis fluid passes through an outer peripheral surface of the hollow fiber membrane, an unnecessary product (waste product) in the blood is removed by dialysis into the dialysis fluid via the hollow fiber membrane. Also, as described later, in priming, the dialysis fluid is backfiltered from outside to inside the hollow fiber membrane, and the backfiltered dialysis fluid flows from the dialysis fluid path to the blood path.

To a distal end of the artery side blood line 14, an artery side puncture needle 20 is connected via a connector 18. The blood pump 22 that is a squeezing type tube pump is provided midway along the artery side blood line 14. The blood pump 22 is driven to normally rotate, and thus squeezes the artery side blood line 14 formed of a flexible tube, thereby feeding blood downstream (toward the dialyzer 12). The blood pump 22 also serves as a valve that closes or opens a part of the artery side blood line 14. Specifically, when the blood pump 22 rotates to feed a fluid, the part of the artery side blood line 14 is opened to allow passage of the fluid, while when the blood pump 22 stops to stop feeding of the fluid, the part of the artery side blood line 14 is closed to block passage of the fluid.

To a distal end of the vein side blood line 16, a vein side puncture needle 26 is connected via a connector 24. An air trap chamber 28 that temporarily stores blood to release air bubbles from the blood is provided midway along the vein side blood line 16. The air trap chamber 28 is a substantially cylindrical container, the vein side blood line 16 being connected near upper and lower ends thereof. The air trap chamber 28 is closed other than a connection port with the vein side blood line 16. Thus, the air trap chamber 28 is a chamber having an internal space closed off from outside air, a so-called airless chamber, and the air trap chamber 28 is filled with blood to its upper end level in dialysis. Also, the air bubbles released from the blood during storage remain near the upper end of the air trap chamber 28. Between the air trap chamber 28 and the connector 24, a valve 41 that opens/closes the vein side blood line 16 is also provided. In a priming processing described later, the valve 41 is closed.

The dialysis fluid supply device 32 includes a dialysis fluid introduction line 34 connected to the dialysis fluid inlet 12c of the dialyzer 12, and a dialysis fluid discharge line 36 connected to the dialysis fluid outlet 12d. The feeding pump 38 and the discharge pump 40 that are tube pumps are provided in the dialysis fluid introduction line 34 and the dialysis fluid discharge line 36, respectively. The two pumps 38, 40 may be driven independently of each other. The two pumps 38, 40 are driven to feed the dialysis fluid to the dialyzer 12 and discharge the dialysis fluid from the dialyzer 12. Like the blood pump 22, the pumps 38, 40 also serve as valves that are driven to open a part of the pipe and stopped to close the part of the pipe.

The vacuum pump 42 is connected between the feeding pump 38 and the dialysis fluid inlet 12c in the dialysis fluid introduction line 34. The vacuum pump 42 is driven to suck air from the dialysis fluid introduction line 34 and a gap communicating with the dialysis fluid introduction line 34, to reduce pressure.

As shown in FIG. 1, the dialysis system 10 further includes a control unit (controller) 11 that controls each component. The control unit 11 controls driving of the various pumps 22, 38, 40, 42 according to an instruction from a user. Also, as described later in detail, if an instruction to perform priming is given by the user, the control unit 11 drives the vacuum pump 42 to produce negative pressure in the gap in the fluid path, and then drives the feeding pump 38 and the blood pump 22 to supply a priming fluid (backfiltered dialysis fluid) into the fluid path.

In dialysis treatment using such a dialysis system 10, the artery side puncture needle 20 and the vein side puncture needle 26 are inserted into a patient, and the blood pump 22, the introduction pump 38, and the discharge pump 40 are driven. Thus, patient's blood collected from the artery side puncture needle 20 flows through the artery side blood line 14 from the blood inlet 12a in the dialyzer 12 into the hollow fiber membrane, while the dialysis fluid flows through the dialysis fluid introduction line 34 from the dialysis fluid inlet 12c to the outer periphery of the hollow fiber membrane.

Then, the blood in the hollow fiber membrane is brought into contact with the dialysis fluid outside the hollow fiber membrane via the hollow fiber membrane, and thus a waste product from the blood is transferred to the dialysis fluid, thereby purifying the blood. The purified blood is led out from the blood outlet 12b to the vein side blood line 16, and returned through the air trap chamber 28 and the vein side puncture needle 26 into the patient's body. The dialysis fluid in which the waste product is mixed is discharged from the dialysis fluid outlet 12d to the dialysis fluid discharge line 36.

Before such dialysis treatment, a priming process is typically performed of passing a priming fluid into the fluid path through which a dialysis fluid or blood flows. The "fluid path" here into which the priming fluid is supplied refers to a path through which a dialysis fluid or blood flows, and in this embodiment, the fluid path includes the artery side blood line 14, the vein side blood line 16, the dialyzer 12, the air trap chamber 28, the dialysis fluid introduction line 34, and the dialysis fluid discharge line 36.

In the priming processing, the control device performs control to drive the feeding pump 38 and drive the blood pump 22 to reversely rotate (driving in a direction opposite to that during treatment).

Thus, the dialysis fluid introduced from the dialysis fluid introduction line 34 is filtered (backfiltered) into the hollow fiber membrane via the hollow fiber membrane in the dialyzer 12, and flows toward the artery side blood line 14 and the vein side blood line 16. In the case of priming using such a backfiltered dialysis fluid, there is no need to connect a separate pipe for supplying the priming fluid to the blood line 14, thereby allowing the priming process to be easily performed. The priming process with the backfiltered dialysis fluid is referred to as "online priming". In this embodiment, online priming is used, but a dedicated pipe for supplying a priming fluid (for example, physiological saline) may be connected to the blood lines 14, 16 to supply the priming fluid through the dedicated pipe.

In the priming process, gaps in the fluid path through which the dialysis fluid and the blood flows (the dialysis fluid introduction line 34, the dialysis fluid discharge lines 36, the blood lines 14, 16, the dialyzer 12, the air trap chamber 28) are desirably all filled with the priming fluid. However, conventionally, air bubbles often remain in the fluid path merely by supplying the priming fluid to the fluid path. In particular, fine air bubbles tend to attach to the inside of the dialyzer 12. Also, air tends to remain in a part of the air trap chamber 28.

To remove air bubbles in a fluid path, a method of applying pressure pulses when supplying a priming fluid, or a method of reducing pressure in a dialyzer during a priming process have been proposed. However, it is difficult to remove air in the fluid path, in particular, air in the dialyzer 12 or the air trap chamber 28, merely by applying the pressure pulses. Also, applying the pressure pulses cannot raise a fluid level in the air trap chamber 28 to an upper surface of the air trap chamber 28. By the method of reducing pressure in the dialyzer during the priming process, pressure cannot be reduced in a gap other than in the dialyzer, for example, a gap in the air trap chamber 28 or the like, and a special facility and process are required to fill the air trap chamber 28 with the priming fluid. Also, for the inside of the dialyzer, in the case of the method of drawing the priming fluid and then reducing pressure, air in the dialyzer is blocked by the priming fluid and not discharged, and thus air in the dialyzer cannot be sufficiently removed. Specifically, it has been conventionally difficult to remove air in the fluid path with a simple configuration and process.

Figure 2:
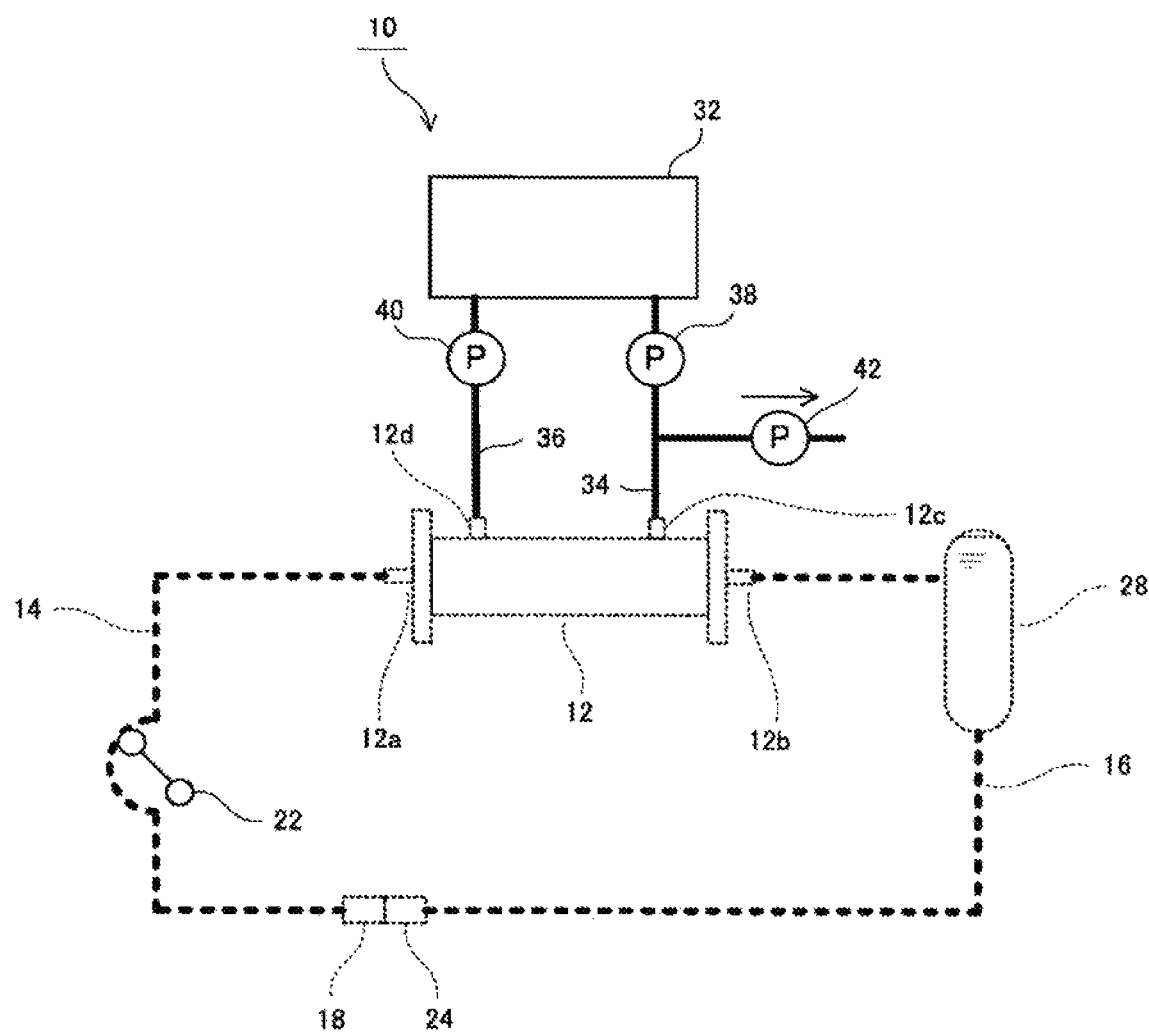
FIG. 2 shows a configuration of the dialysis system during performance of priming.

Thus, in this embodiment, a pressure reduction process is performed of reducing pressure in the gap in the fluid path to negative pressure before supply of the priming fluid. Then, to facilitate the pressure reduction process, the vacuum pump 42 is connected to the dialysis fluid introduction line 34. With reference to FIG. 2, a flow of the pressure reduction process will be described below. An arrow in FIG. 2 shows a driving direction (sucking direction) of the pump in the pressure reduction process.

In performing the pressure reduction process, as shown in FIG. 2, the connector 18 of the artery side blood line 14 and the connector 24 of the vein side blood line 16 are first connected to provide communication between flow paths of the lines. Further, driving of the blood pump 22, the feeding pump 38, and the discharge pump 40 is stopped so that the artery side blood line 14, the dialysis fluid introduction line 34, and the dialysis fluid discharge line 36 are all closed off from the outside air. Thus, the fluid path is a closed space cut off from the outside air.

In such a state, the vacuum pump 42 is then driven to suck the air in the fluid path to reduce pressure in the gap in the fluid path. The vacuum pump 42 is driven to produce negative pressure in the lines 14, 16, 34, 36, the dialyzer 12, and the air trap chamber 28. The control unit determines that negative pressure is produced in the gap in the fluid path after the vacuum pump 42 reduces pressure for a certain time, and stops driving of the vacuum pump 42. Of course, a pressure sensor that detects pressure in the fluid path may be separately provided to control driving of the vacuum pump 42 according to a detection result of the pressure sensor.

After the pressure reduction by the vacuum pump 42 is finished, the priming process is performed of introducing the dialysis fluid as the priming fluid into the fluid path. For introducing the dialysis fluid, the vacuum pump 42 is stopped, and the feeding pump 38 is driven in a normal direction (a direction of feeding the dialysis fluid into the dialyzer 12). Thus, the dialysis fluid introduced from the dialysis fluid introduction line 34 is backfiltered by the hollow fiber membrane in the dialyzer 12, and flows toward the artery side blood line 14 and the vein side blood line 16. At this time, negative pressure is produced in the dialyzer 12, the air trap chamber 28, the artery side blood line 14, and the vein side blood line 16, and no air exists therein, and thus no air bubbles remain even if the dialysis fluid (priming fluid) is supplied. Since the negative pressure is produced in the air trap chamber 28, the air trap chamber 28 may be filled with the dialysis fluid (the fluid level may be raised to the upper end of the air trap chamber 28) simply by introducing the dialysis fluid without any special processing. Thus, the priming process of filling the fluid path with the dialysis fluid is finished. After the priming process is finished, the connectors 18, 24 are disconnected, and the artery side puncture needle 20 and the vein side puncture needle 26 are attached to the connectors 18, 24 and inserted into the patient to perform dialysis treatment.

The applicant conducted an experiment in which the discharge pump 40 or the like instead of the vacuum pump 42 was driven for 5 or 15 minutes to reduce pressure in the gap in the fluid path. In the case of driving the discharge pump 40 for 5 minutes, pressure in the gap could be reduced to about −500 mmHg. When the priming fluid was then introduced, no air bubbles remained, and a satisfactory result was obtained. In the case of driving the discharge pump 40 for 15 minutes, pressure in the gap could be reduced to about −700 mmHg. Also in this case, when the priming fluid was then introduced, no air bubbles remained, and a satisfactory result was obtained. The vacuum pump 42 seems to be able to more efficiently reduce pressure than the discharge pump 40, and thus it is supposed that negative pressure of about −750 mmHg is reached by driving for about one minute, although this depends on performance of the vacuum pump 42.

Figure 3:
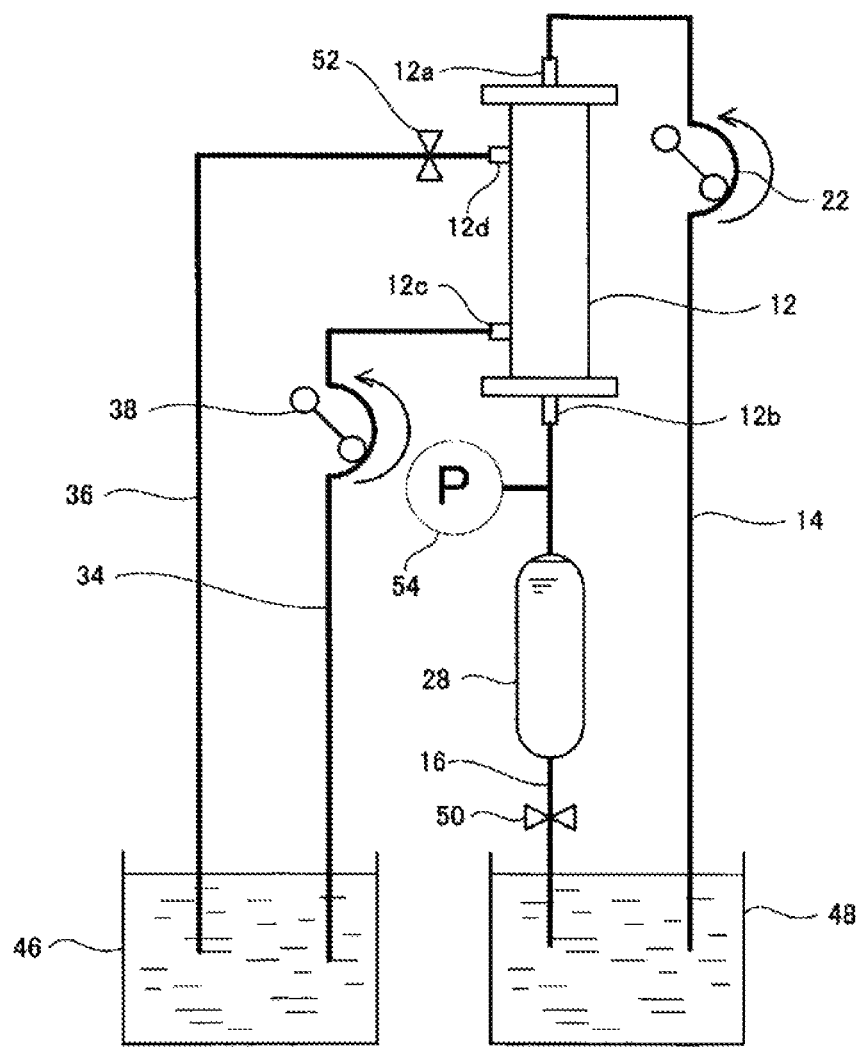
FIG. 3 shows a configuration of an experiment device used for a verification experiment.
Figure 5:
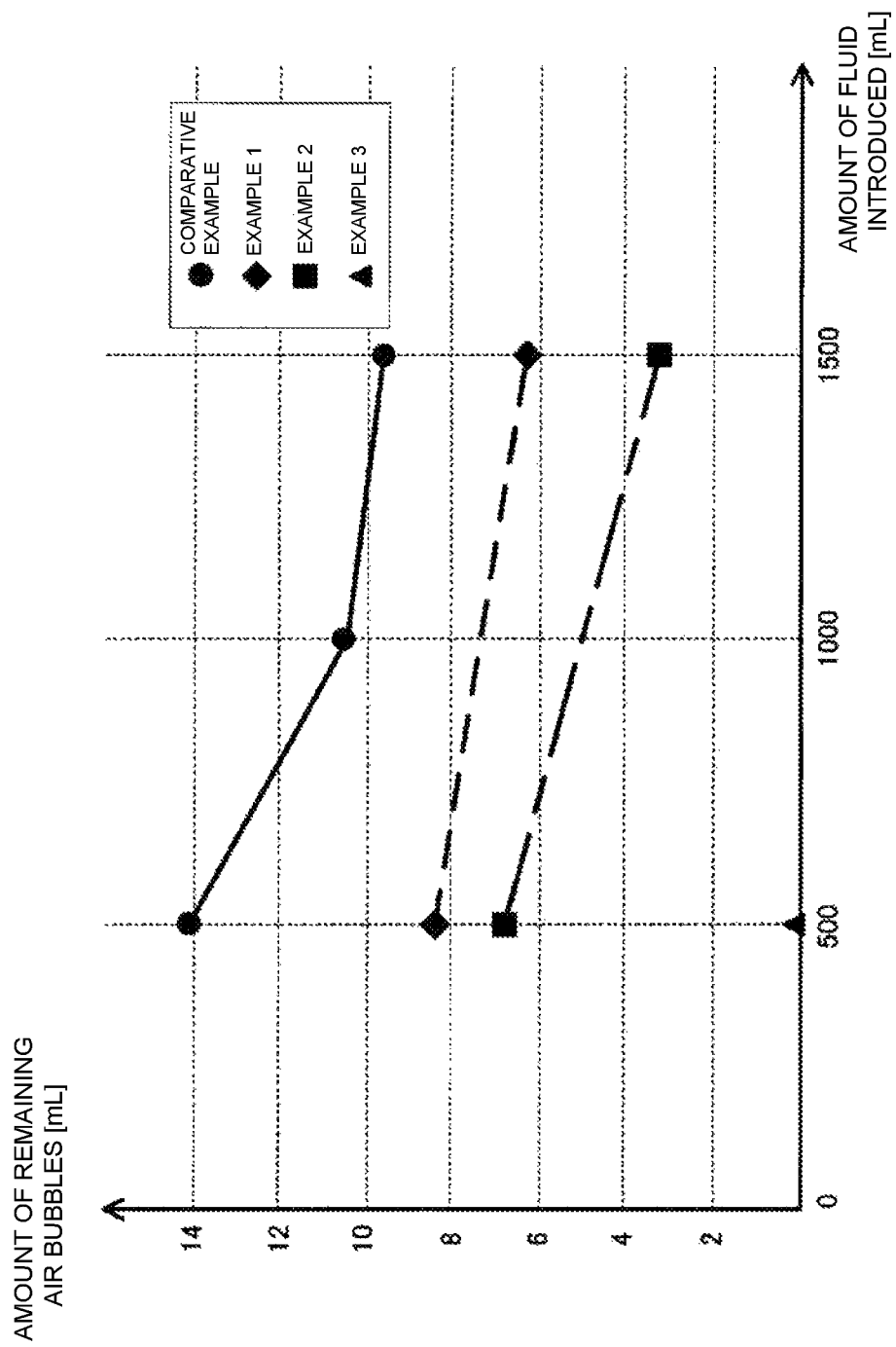
FIG. 5 is a graph showing results of the verification experiment.

Next, an experimental result of this embodiment will be described. FIG. 3 shows a configuration of an experiment device used for a verification experiment in this embodiment. FIG. 4 is a table showing contents of the verification experiment, and FIG. 5 is a graph showing results of the verification experiment. In FIG. 3, arrows near the pumps 22, 38 show directions of normal driving of the pumps 22, 38. In the verification experiment, tanks 46, 48 filled with water were prepared. Then, the distal ends of the artery side blood line 14 and the vein side blood line 16 were placed in communication with the water in the tank 46, and the dialysis fluid introduction line 34 and the dialysis fluid discharge line 36 were placed in communication with the water in the tank 48. The discharge pump 40 was omitted, and instead, a first test valve 50 and a second test valve 52 were provided in the vein side blood line 16 and the dialysis fluid discharge line 36. Further, like the blood pump 22, the feeding pump 38 is a roller pump that squeezes a tube to feed a fluid. Further, a pressure sensor 54 is provided between the dialyzer 12 and the air trap chamber 28.

In the verification experiment, the experiment device is used to perform priming, and then measure an amount of air bubbles remaining in the fluid path. As shown in FIGS. 3 and 4, in Example 1, the first test valve 50 and the second test valve 52 are closed to seal the fluid path, and in that state, reverse driving of the blood pump 22 and reverse driving of the feeding pump 38 are performed to reduce pressure in the fluid path to −300mmHg (STEP 1). After the pressure is reduced to −300mmHg, with the first test valve 50 being opened, reverse driving of the blood pump 22 and normal driving of the feeding pump 38 are performed to introduce water from the tank 48 into the fluid path, in particular, the dialyzer 12 and the blood lines 14, 16 (STEP 2). An amount of fluid introduced at this time is 500 mL or 1500 mL. A remainder of the water having passed through the fluid path is released into the tank 46. Then, with the first test valve 50 being closed and the second test valve 52 being opened, the blood pump 22 is stopped and the feeding pump is normally driven to introduce water from the tank 48 into the fluid path, in particular, the dialyzer 12 and the dialysis fluid discharge line 36 (STEP 3). An amount of fluid introduced at this time is 500 mL. A remainder of the water having passed through the fluid path is released into the tank 48.

Also in Examples 2, 3, STEPS 1 to 3 as in Example 1 are performed. However, in STEP 1, pressure is reduced to −500 mmHg in Example 2 and to −700 mmHg in Example 3.

In a Comparative Example, without pressure reduction before priming, the same processes as in STEPS 2 and 3 in Examples 1 to 3 are performed. Specifically, in the table in FIG. 4, STEPS 1 and 2 in Comparative Example are substantially the same as STEPS 2 and 3 in Examples 1 to 3. However, in Comparative Example, an amount of fluid first introduced is 500 mL or 1000 mL or 1500 mL.

The amount of air bubbles is measured in the following procedure. For each of Examples and Comparative Example, when defined STEPS are finished, the fluid level in the air trap chamber 28 is set to a defined level. Then, the dialyzer 12 is inverted so that the blood outlet 12b connected to the air trap chamber 28 is located above the blood inlet 12c. In that state, the blood pump 22 is driven at the highest speed. Further, outer walls of the dialyzer 12, the artery side blood line 14, and the vein side blood line 16 are tapped to release air bubbles attached to inner walls thereof, and the air bubbles are collected in the air trap chamber 28. Finally, an amount of reduction of the fluid level in the air trap chamber 28 is measured, and an amount of remaining air bubbles is measured from the amount of reduction.

FIG. 5 is a graph showing results of the verification experiment, the abscissa represents an amount of fluid first introduced (STEP 2 in Examples 1 to 3 and STEP 1 in Comparative Example), and the ordinate represents an amount of remaining air bubbles after the experiment is finished. In Example 3 with the amount of fluid introduced of 1500 mL, the amount of remaining air bubbles was too small to be measured, and thus a value thereof is not shown in FIG. 5.

As is apparent from FIG. 5, it is found that the amount of remaining air bubbles is reduced to about 60% in Example 1 in which pressure is previously reduced to −300 mmHg compared to the Comparative Example in which pressure is not previously reduced. Further, the amount of remaining air bubbles is reduced to 48% (the amount of fluid introduced of 500 mL) or 33% (the amount of fluid introduced of 1500 mL) in Example 2 in which pressure is previously reduced to −500 mmHg compared to the Comparative Example. Further, it is found that previously reducing the pressure to −700 mmHg may reduce an amount of remaining fluid to about zero (1 mL or less).

As is apparent from the above description, according to this embodiment, the pressure in the gap in the fluid path is previously reduced to negative pressure before supply of the priming fluid into the fluid path. This can easily and reliably prevent air bubbles from remaining when the priming fluid is supplied. Also, the fluid level in the air trap chamber 28 may be raised to the upper end thereof without any special processing.

Figure 6:
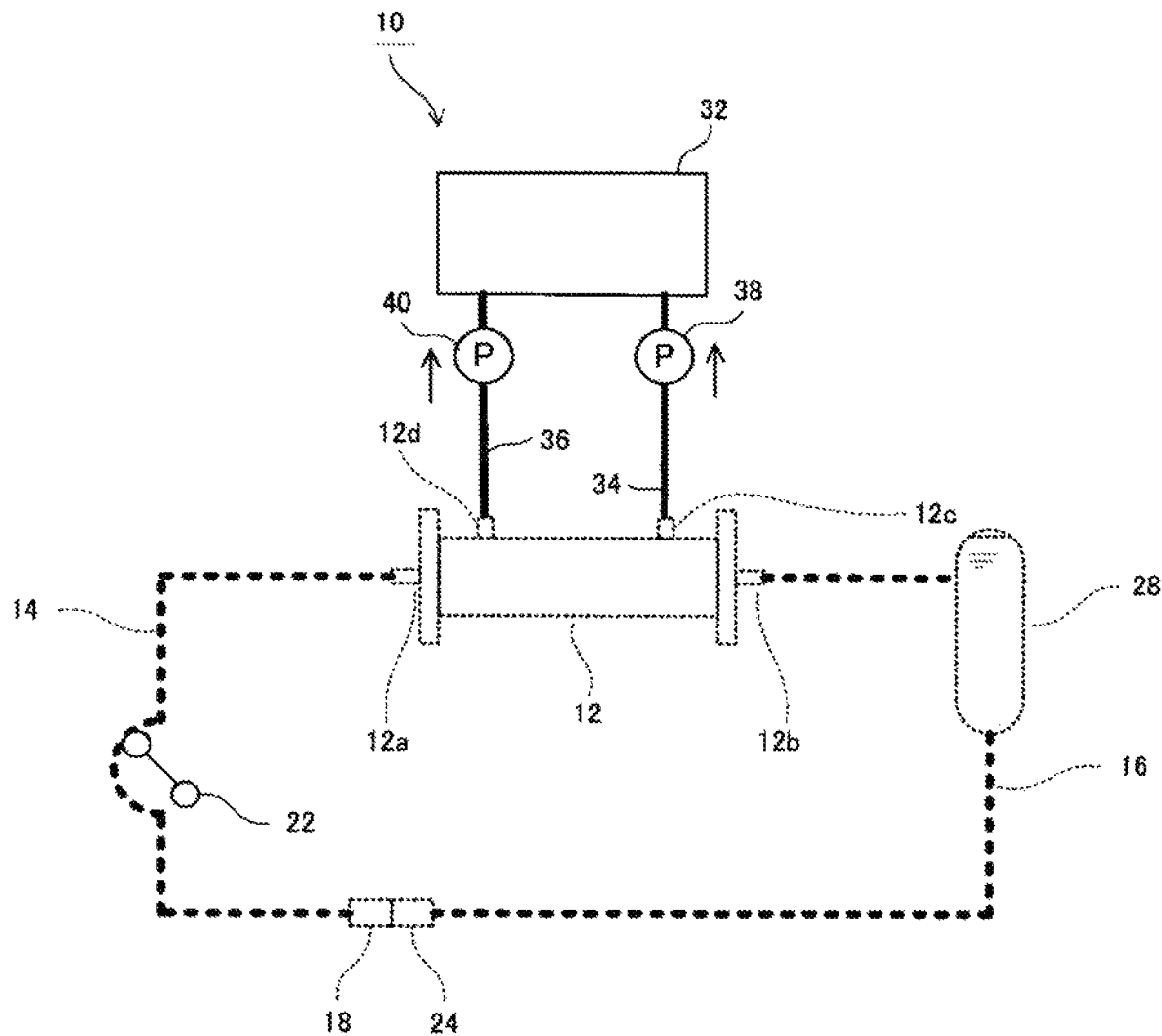
FIG. 6 shows a configuration of a different dialysis system.

The configuration described here is an example, and as long as pressure in the gap in the fluid path may be reduced before supply of the priming fluid, other configurations may be changed as appropriate. For example, in this embodiment, the vacuum pump 42 is driven to reduce pressure, but a different pump, for example, the blood pump 22 or the discharge pump 40, may be driven to reduce pressure. For example, before supply of the priming fluid, the discharge pump 40 may be driven in addition to or instead of driving of the vacuum pump 42, thereby reducing pressure in the gap in the fluid path. Also, in addition to or instead of driving of the vacuum pump 42 or the discharge pump 40, the feeding pump 38 may be reversely driven (driven in a direction of sucking the fluid from the dialyzer 12) to reduce pressure in the gap in the fluid path. FIG. 6 shows an example of a configuration in which the discharge pump 40 instead of the vacuum pump 42 is driven and/or the feeding pump 38 is reversely driven to reduce pressure in the gap in the fluid path. In FIG. 6, arrows near the pumps 40, 38 show a driving direction (sucking direction) in the pressure reduction process.

Figure 7:
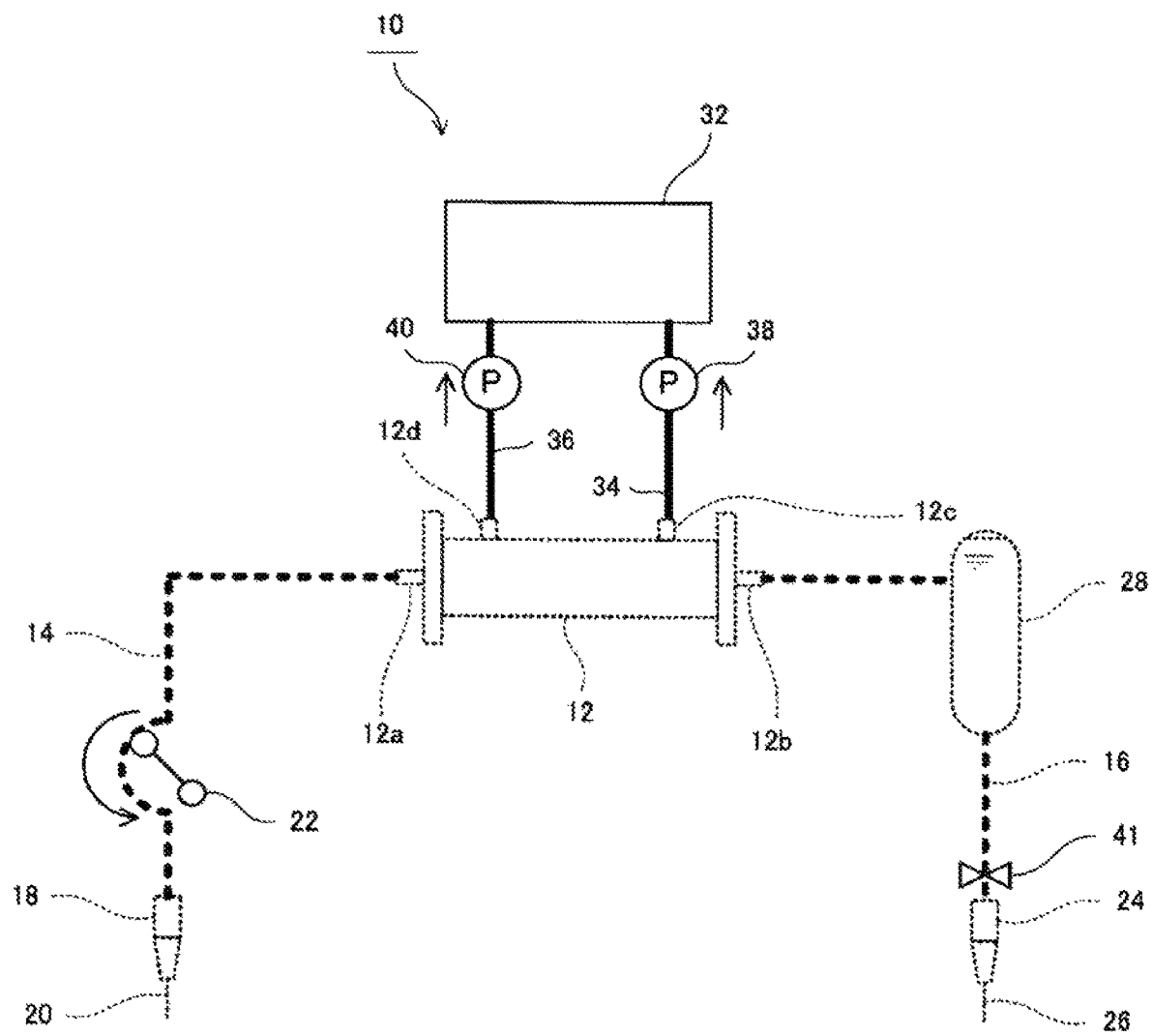
FIG. 7 shows a configuration of a different dialysis system.

Further, in addition to or instead of driving of the vacuum pump 42 or the discharge pump 40 or reverse driving of the feeding pump 38, the blood pump 22 may be reversely driven (driven in the direction of sucking the fluid from the dialyzer 12) to reduce pressure in the gap in the fluid path. FIG. 7 shows an example of a configuration in which with the valve 41 being closed, the blood pump 22 instead of the vacuum pump 42 is reversely driven (driven in the direction of sucking the fluid from the dialyzer 12) to reduce pressure in the gap in the fluid path. In this case, the distal end of the artery side blood line 14 is not connected to the vein side blood line 16 but is placed in communication with outside air. Also, at the distal end of the vein side blood line 16, a member is provided that closes or uncloses communication between the vein side blood line 16 and the outside air, for example, a valve that is opened/closed according to an instruction from the control unit, a clamp that is manually opened/closed, a sealing cap attached to a distal end of the puncture needle 26, or the like. In the configuration in FIG. 7, simultaneously with the reverse driving of the blood pump 22, the discharge pump 40 may be driven and/or the feeding pump 38 may be reversely driven. In FIG. 7, arrows near the pumps 22, 38, 40 show a driving direction (sucking direction) in the pressure reduction process.

Figure 8:
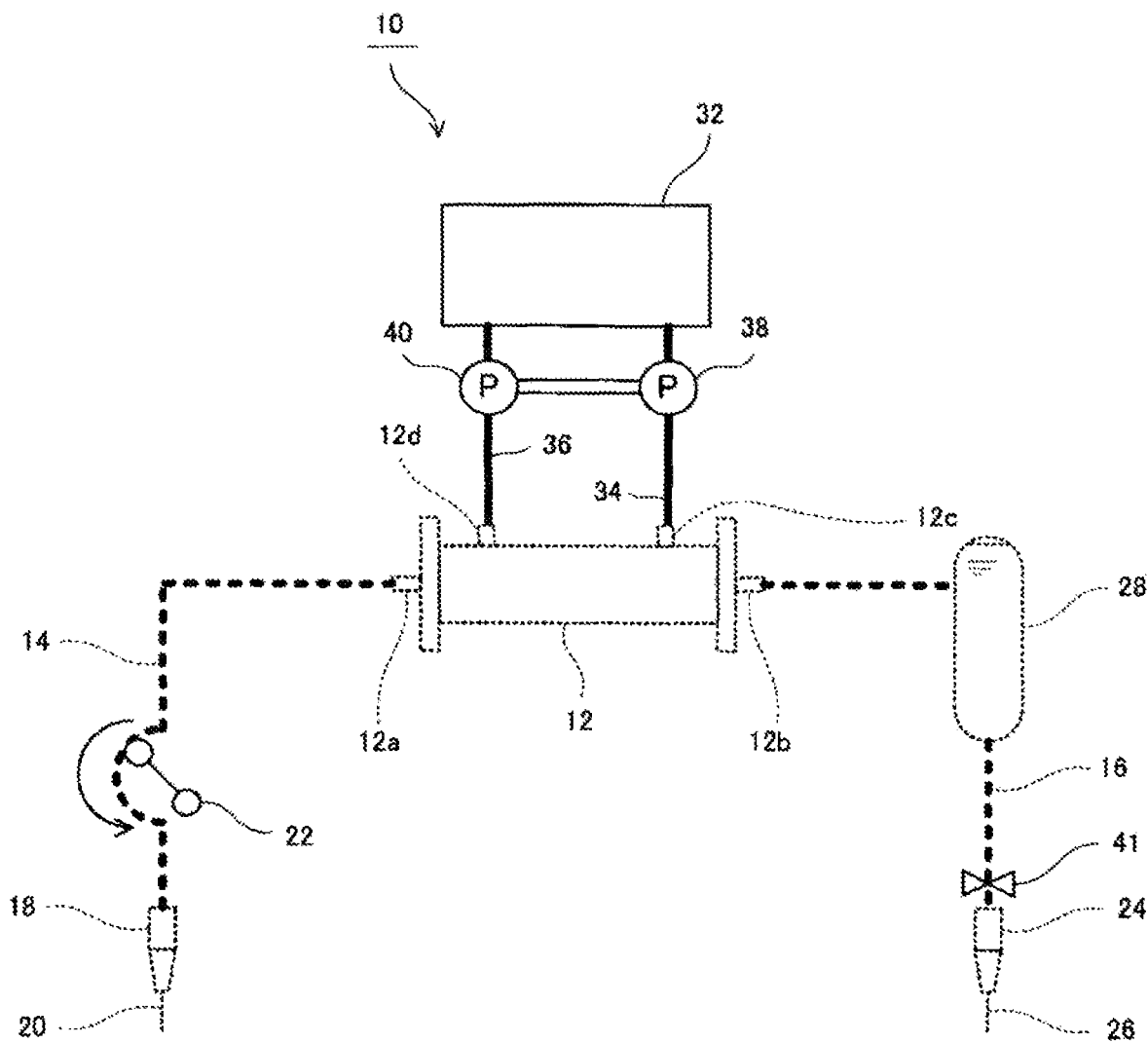
FIG. 8 shows a configuration of a different dialysis system.

In this embodiment, the feeding pump 38 and the lead-out pump 40 are tube pumps driven independently of each other, but the feeding pump 38 and the lead-out pump 40 may be formed as a dual pump such that the feeding pump 38 and the lead-out pump 40 are driven in conjunction with each other. FIG. 8 shows an example of the feeding pump 38 and the lead-out pump 40 formed as a dual pump. In this case, pressure may not be reduced by reverse driving of the feeding pump 38 and driving of the lead-out pump 40. Thus, to reduce pressure in the gap in the fluid path when the dual pump is used, the blood pump 22 is reversely driven with the valve 41 being closed, or the vacuum pump 42 separately provided (not shown in FIG. 8) is driven. In FIG. 8, an arrow near the pump 22 shows a driving direction (sucking direction) in the pressure reduction process.

In this embodiment, the blood pump 22, the feeding pump 38, and the lead-out pump 40 that are tube pumps are used as valves, but a valve that is opened/closed according to an instruction from the control unit may be separately provided. In this embodiment, the online priming for performing priming with the backfiltered dialysis fluid is exemplified, but the technology in this embodiment is applicable to a case where a priming fluid (for example, physiological saline or the like) is supplied via a dedicated pipe connected to the artery side blood line 14 or the vein side blood line 16.

Figure 9:
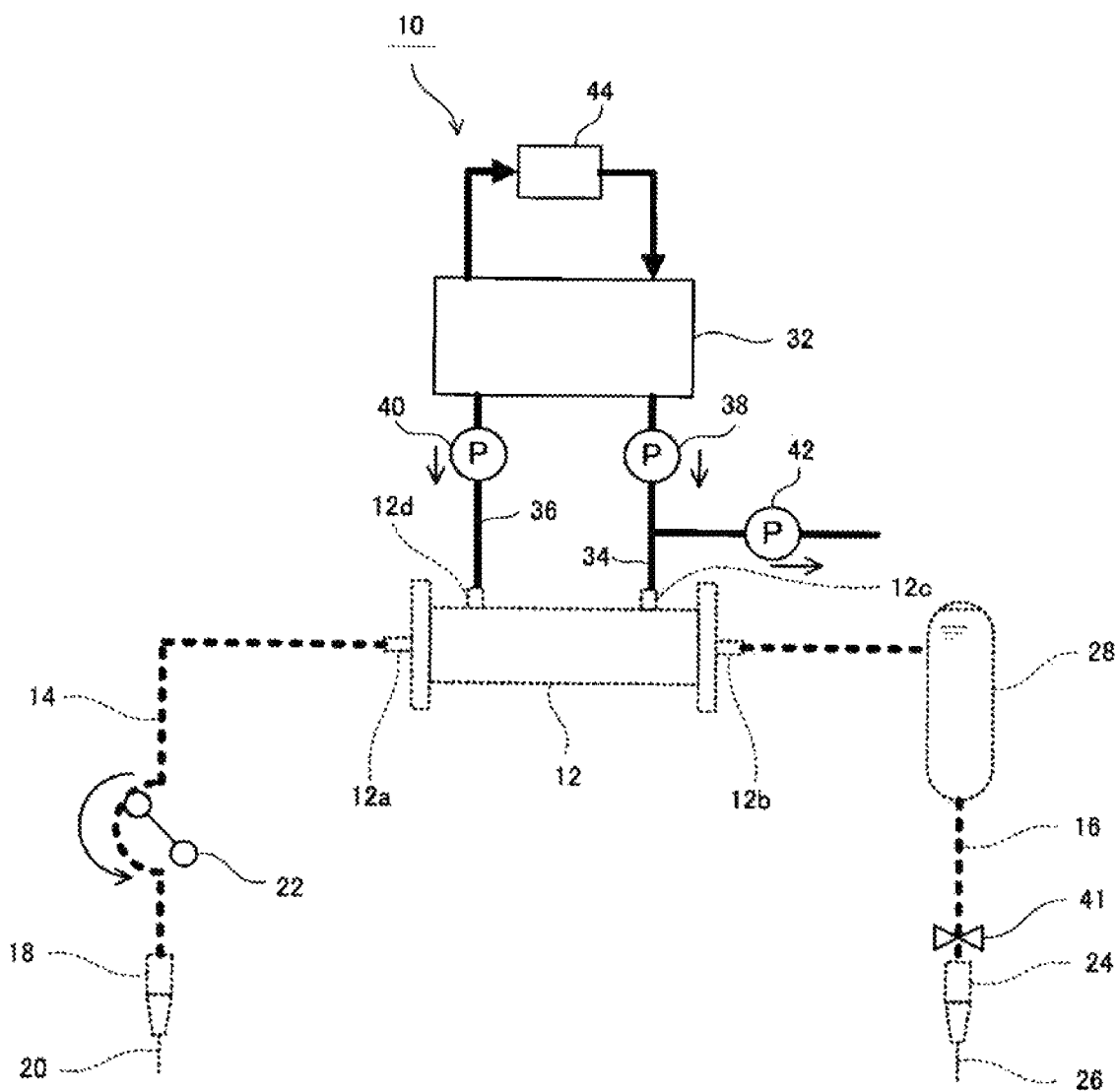
FIG. 9 shows a configuration of a different dialysis system.

Also, as shown in FIG. 9, the dialysis system 10 may further include a dialysis fluid regeneration column 44. Specifically, the dialysis fluid having passed through the dialyzer 12 is typically returned to the dialysis fluid supply device 32 and then discharged to the outside. On the other hand, a new dialysis fluid is supplied from outside to the dialysis fluid supply device 32. The dialysis fluid regeneration column 44 reproduces an unnecessary product contained in a used dialysis fluid, which is typically discarded, by causing an adsorbent to adsorb the product and so on, and returns a reproduced dialysis fluid to the dialysis fluid supply device 32. Specifically, in the configuration in FIG. 9, the dialysis fluid is circulated by the dialysis fluid regeneration column 44. When the dialysis fluid regeneration column 44 is used, priming of an inside of the dialysis fluid regeneration column is also desirably performed before start of the dialysis. However, the adsorbent included in the dialysis fluid regeneration column 44 is a porous material, and it has been conventionally difficult to fill minute holes in the adsorbent with the priming fluid. With the configuration in which pressure is reduced before priming, as in this embodiment, the inside of the dialysis fluid regeneration column 44 may be filled with the priming fluid.

When the pressure reduction processing is performed in the configuration in FIG. 9, with the dialysis fluid supply unit 32 and the dialysis fluid regeneration column 44 being empty (not filled with the dialysis fluid), the feeding pump 38 is driven and/or the lead-out pump 40 is reversely driven to reduce pressure in the dialysis fluid regeneration column 44. Subsequently or simultaneously, the vacuum pump 42 is driven and/or the blood pump 22 is reversely driven to reduce pressure in the dialyzer 12 and the blood lines 14, 16. In FIG. 9, arrows near the pumps 22, 38, 40, 42 show a driving direction (sucking direction) in the pressure reduction process. When the pressure reduction process is finished, a bag filled with the dialysis fluid is connected to the fluid path or the like between the dialysis fluid supply unit 32 and the dialysis fluid regeneration column 44 to introduce the dialysis fluid into the fluid path. Thus, the priming of the fluid path including the dialysis fluid regeneration column 44 is performed using the dialysis fluid. Physiological saline may be used instead of the dialysis fluid.

In the description above, the dialysis system 10 having an airless chamber cut off from the outside air is exemplified, but the air trap chamber 28 may be a typical air trap chamber opened to the outside air. The air trap chamber 28 may be omitted if measures against air bubbles can be ensured. In this embodiment, the dialyzer 12 is exemplified as an example of the blood purifier, but a different blood purifier may be used. For example, a blood purification column that includes an adsorbent for adsorbing a disease agent contained in blood and purifies the blood may be used as the blood purifier. In this case, there is no need to supply the dialysis fluid, and the need for the dialysis fluid introduction line 34, the dialysis fluid discharge line 36, the feeding pump 38, and the discharge pump 40 is eliminated. Thus, in this case, the blood pump 22 is reversely driven or the vacuum pump 42 connected midway along the blood lines 14, 16 is driven to reduce pressure. When the blood purification column is used, the dialysis fluid is not used. Thus, a bag filled with physiological saline is connected to the blood lines 14, 16 in priming to introduce the physiological saline into the fluid path. The technology in this embodiment is applicable not only to the dialysis system, but also to other blood purification devices that require a previous priming process, for example, an apheresis device, a continuous renal replacement therapy (CRRT) device or the like.

REFERENCE SIGNS LIST

10 dialysis system
12 dialyzer
14 artery side blood line 16 vein side blood line
18, 24 connector
20 artery side puncture needle
22 blood pump
26 vein side puncture needle
28 air trap chamber
32 dialysis fluid supply unit
34 dialysis fluid introduction line
36 dialysis fluid discharge line
38 feeding pump
40 discharge pump
42 vacuum pump
44 dialysis fluid regeneration column
46, 48 tank
50 first test valve
52 second test valve

The invention claimed is:

1. A blood purification device for purifying blood drawn from a body and then returning the blood into the body, the blood purification device comprising:
at least one pump arrangement disposed in a fluid path through which blood or a dialysis fluid flows;
at least one valve disposed in the fluid path and closes or opens a part of the fluid path;
a dialysis fluid supply device supplying dialysis fluid to the fluid path, the fluid path including (i) at least a dialyzer for purifying the blood, (ii) a blood line through which the blood flows, and (iii) a dialysis fluid line through which the dialysis fluid flows; and
a controller connected to the at least one pump arrangement and the at least one valve, the controller being configured to control operation of the at least one pump arrangement and the at least one valve, the controller, the at least one pump arrangement, and the at least one valve being configured to cause the blood purification device to perform:
a pressure reduction process of reducing a pressure in a gap in the fluid path to a negative pressure state by controlling the at least one pump arrangement and the at least one valve,
after performing the pressure reduction process, a priming process of controlling driving of the at least one pump arrangement and the at least one valve to operate to cause a priming fluid to be output from the dialysis fluid supply device such that the dialysis fluid introduced from the dialysis fluid supply device is back-filtered into the dialyzer through the dialysis fluid line, and then flows toward the blood line, and
after performing the pressure reduction process and the priming process, a blood purification process of controlling the at least one pump arrangement and the at least one valve to supply the blood or the dialysis fluid through the fluid path to perform blood purification.

2. The blood purification device according to claim 1, wherein the fluid path further includes an air trap chamber.

3. The blood purification device according to claim 1, wherein the dialyzer includes a blood purification membrane and purifies blood with the blood purification membrane.

4. The blood purification device according to claim 1, wherein the at least one pump arrangement includes a blood pump that feeds the blood to the dialyzer, a feeding pump that feeds the dialysis fluid to the dialyzer, and a discharge pump that discharges the dialysis fluid from the dialyzer, and
the controller is configured to drive the at least one valve to close off the fluid path from outside air, and then perform at least one of three functions: reverse driving of the blood pump, driving of the discharge pump, and reverse driving of the feeding pump to reduce pressure in the gap.

5. The blood purification device according to claim 1, further comprising a dialysis fluid regeneration column that reproduces the dialysis fluid having passed through the dialyzer and returns the dialysis fluid to the dialyzer to circulate the dialysis fluid.

6. The blood purification device according to claim 1, wherein the at least one pump arrangement includes a vacuum pump located along the fluid path, the vacuum pump being configured to suction air in the fluid path, and the vacuum pump is configured to not feed the dialysis fluid or the blood into the dialyzer, and
the controller is configured to drive the at least one valve to close off the fluid path from outside air, and then drive the vacuum pump to reduce pressure in the gap.

7. A priming method comprising:
providing at least one pump arrangement disposed in a fluid path through which blood or a dialysis fluid flows, and at least one valve disposed in the fluid path that closes or opens a part of the fluid path;
supplying dialysis fluid to the fluid path by a dialysis fluid supply device, the fluid path including (i) at least a dialyzer for purifying the blood, (ii) a blood line through which the blood flows, and (iii) a dialysis fluid line through which the dialysis fluid flows;
reducing, by a controller connected to and controlling operation of the at least one pump arrangement and the at least one valve, a pressure in a gap in the fluid path to a negative pressure state by controlling the at least one pump arrangement and the at least one valve;
after reducing the pressure in the gap, controlling driving of the at least one pump arrangement and the at least one valve to operate to cause a priming fluid to be output from the dialysis fluid supply device such that the dialysis fluid introduced from the dialysis fluid supply device is back-filtered into the dialyzer through the dialysis fluid line, and then flows toward the blood line; and
after both reducing the pressure in the gap and causing the priming fluid to be output from the dialysis fluid supply device, controlling the at least one pump arrangement and the at least one valve to supply the blood or the dialysis fluid through the fluid path to perform blood purification.

* * * * *